United States Patent
Hukari et al.

(10) Patent No.: US 7,781,206 B2
(45) Date of Patent: Aug. 24, 2010

(54) SYSTEMS AND METHODS FOR EFFECTING A PHYSICAL CHANGE IN A BIOLOGICAL SAMPLE

(75) Inventors: Kyle W. Hukari, San Ramon, CA (US); Jason A. A. West, Castro Valley, CA (US)

(73) Assignee: Arcxis Biotechnologies, Pleasanton, CA (US)

( * ) Notice: Subject to any disclaimer, the term of this patent is extended or adjusted under 35 U.S.C. 154(b) by 715 days.

(21) Appl. No.: 11/402,656

(22) Filed: Apr. 11, 2006

(65) Prior Publication Data
US 2007/0238090 A1    Oct. 11, 2007

(51) Int. Cl.
*C12M 1/00*    (2006.01)
(52) U.S. Cl. .................. 435/289.1; 435/375; 435/173.1
(58) Field of Classification Search ........................ None
See application file for complete search history.

(56) References Cited

U.S. PATENT DOCUMENTS 6,695,317 B2 *   2/2004   Lehnert et al. ............... 277/436
2002/0187547 A1 *   12/2002   Taylor et al. ............. 435/306.1

* cited by examiner

*Primary Examiner*—James S Ketter
(74) *Attorney, Agent, or Firm*—Woodcock Washburn, LLP (57) ABSTRACT

The present invention relates generally to systems and methods for processing a biological sample that result in a physical change, such as reacting two molecules together to form a reaction product or for use in lysing viruses or biological cells for analysis using biological assay systems. As such, the present invention relates both to breaking apart biological species such as viruses and cells, as well as the formation of reactants from one or more reactive species. The sample has a volume in the range from about 1 microliter to 10 milliliters. The sample is processed by applying pressure, and either sonic energy or thermal energy to the sample, wherein the pressure achieved is usually at least 24 atmospheres, and the temperature of the sample is usually raised to at least 50° C.

24 Claims, 7 Drawing Sheets

SYSTEMS AND METHODS FOR EFFECTING A PHYSICAL CHANGE IN A BIOLOGICAL SAMPLE

The present invention relates generally to systems and methods for processing a biological sample that result in a physical change, such as reacting two molecules together to form a reaction product or for use in lysing viruses or biological cells for analysis using biological assay systems. As such, the present invention relates both to breaking apart biological species such as viruses and cells, as well as the formation of reactants from one or more reactive species.

In one embodiment of the present invention, certain biological samples containing cellular components must be pretreated in order to disrupt the cell wall and release intracellular components for preparation of samples for analysis. This treatment procedure is generally known as "lysis", and various methods of lysing are known in the field. The lysis of robust cellular components, such as microbial spores, can be difficult. Spores are the most difficult species to lyse because of their strong exterior wall, which allows them to survive extremes of the environment and remain viable.

One of the most common methods used to lyse robust cellular species involves the use of sonication, which causes pressure transduction, or "cavitation" of the sample. This method utilizes high frequency energy waves to break apart the walls of the cells. This is an effective method for partially lysing cells, but it does not always result in complete lysis, solubilization and inactivation of the species in question. One method for sonication is to place the sample in a single use container with no moving parts, and to introduce sonic waves into the container. The main disadvantages of this method are the incomplete lysis and solubilization of the cells in the biological sample, and the generation of aerosols and bubbles. This presents a significant hazard to the user, as intact aerosolized biological agents create the greatest risk for toxic or infectious exposure. Since there is no guarantee that the agent is fully inactivated by this simple method, it may still be hazardous to the user.

Another problem with using sonication alone is that some cellular species require large amounts of energy to be introduced in order to inactivate and lyse the cells in a biological sample. The most common example of this is bacterial spores. The most effective way to introduce the sonic energy into the sample is by using a sonic probe, which comes into direct contact with the sample. This is most often done in an open container, for easy access to the sample. This is particularly dangerous, because as the sample is sonicated, a large portion will be released into the air. Also, a large amount of energy will be needed in order to effectively complete the lysis, which may result in heating of the sample and inactivation of the cellular components of interest.

Accordingly, there is a need for systems and methods to pretreat biological samples that are safe and easy to use, and produce a suitable yield of the biological components of interest.

SUMMARY OF THE INVENTION

It is an object of the present invention to provide systems and methods for pretreating biological samples and particularly for lysing of viruses and cells in biological samples or for providing the energy necessary to carry out a reaction between two chemical species or within a chemical species.

According to one aspect of the present invention, a method of effecting a physical change in a biological sample is provided, which comprises the steps of: placing the sample (for example, 1 microliter to 10 milliliters, or 1 microliter to 1 milliliter) in a sample chamber having at least one opening; inserting a plug into the opening to seal the chamber; applying a pressure of at least 30 psi (for example, 350 psi to 500 psi) to the chamber; and applying either thermal energy (for example, above 50° C., or 50° C. to 200° C., or 100° C. to 250° C.) or sonic energy, or both sonic energy and thermal energy, to the sample.

The sample may be known to contain or may be suspected of containing cells, subcellular structures like mitochondria, or acellular particles, such as macromolecular complexes, liposomes, vesicles, beads, or a combination thereof. In other aspects, the particle is a solid that has a compound chemically bonded to the surface thereof.

The pressure may be varied simply by adjusting the depth to which the plug is inserted into the chamber, or the pressure may be adjusted by regulating the gaseous pressure above the sample chamber. Additionally, the sonic energy may be supplied in the form of a sonication probe or by applying ultrasound waves. If a sonication probe is used, it may or may not come in direct contact with the sample.

To optimize the reaction conditions during the procedure, either or both the pressure and the temperature may be monitored and adjusted as necessary to be increased, decreased, cycled or kept constant.

In one embodiment, the method is performed in a multi-well plate holding a plurality of samples.

In another embodiment of the invention, the method is used for lysis, with the combination of pressure and sonication resulting in biological molecules being released from cells in the sample to form a lysate. The initial pressure applied to the sample may be around 30 psi, and the sample may be heated to a temperature sufficient to increase the pressure to at least 24 atmospheres (350 psi).

According to another aspect of the invention, a system is provided for practicing the method which comprises: a sample container having at least one chamber for containing the sample, the chamber having at least one opening; a plug adapted for sealing the opening of the chamber and for applying pressure to the chamber; a securing device for securing the plug in the chamber.

Other aspects of the invention are described throughout the specification

DETAILED DESCRIPTION OF THE INVENTION

The drawings illustrate various embodiments of a system that can be used to effect a chemical change in a biological sample. By way of example, a system that is useful to lyse and solubilize a biological sample containing robust components such as spores is depicted and described herein. However, it should be understood that such a system is also useful for providing the energy necessary to effect the reaction between and among chemical species, such as the formation of a reaction product from two starting components or the breaking apart of a chemical species or multi-species complex, such as a liposome or subcellular structure. The disclosed technology enables researchers and other interested parties to make lysates from cell-containing biological samples or a solubilized mix of proteins, DNA, and any other extra or intracellular macromolecules from variety of organism and cell types, including viruses, bacteria (prokaryotic), bacterial spores, plant cells, and eukaryotic (mammalian) cells. The systems and methods described herein can be used to provide extracts of proteins and nucleic acids in an amount sufficient to allow further characterization or experimentation with such extracts.

As used herein, the term "biological sample" refers to material of a biological origin, which may be a body fluid, tissue sample, research sample containing biomolecules, and which also be from an environmental source, a body of water, etc., and which may optionally contain or be suspected of containing single-celled and/or multicellular organisms. Such samples may include organs, tissues, cells, spores, organelles, molecular aggregates such as hybridized nucleic acids and aggregated proteins, single molecules, as well as portions thereof, and combinations thereof. For example, prokaryotic cells, eukaryotic cells and any combinations thereof can be included in the biological sample, such as cells from microorganisms, animals and plants. In particular, the biological sample includes bacterial cells, bacterial spores, viruses, prions, eukaryotic cells (blood cells, tissue, white cells), bone marrow, bone, or any combination thereof.

The term "cell", as used herein, is intended to encompass prokaryotic cells, eukaryotic cells, phage particles, and organelles.

The terms "lysate" or "cell lysate", as used herein, refer to a composition comprising at least some cells that have ruptured cell walls and/or cell membranes.

As used herein, the term "lysing," with reference to a cell suspension, refers to rupturing the cell walls and/or cell membranes, cellular components, organelles of at least a portion of the cells such that at least part of the contents, e.g. biological molecules of the cells are released. In certain embodiments of the method of the present invention, at least a portion of the biological material is lysed to form a lysate. Without being bound by any particular theory of operation, the biological sample lyses under physico-chemical forces created by the combination of the appropriate solvent environment, along with pressure and either heat or cavitation, or a combination of the two. Biological molecules that are released upon lysing include nucleic acids, carbohydrates, amino acids, proteins, peptides, DNA, RNA, and any combination thereof. Biological samples are typically aqueous, which means they contain an effective amount of water molecules to cause them to be in the liquid state.

As used herein, the term "lysate" refers to the products of lysing biological material, for example, the biological molecules that are released as listed above. Although most lysates will be readily soluble in the biological sample fluid, certain lysate portions, such as hydrophobic components, may require additional steps to ensure at least a portion of the lysate is solubilized. Examples of additional steps for ensuring solubilization of the lysates include a suitable surfactant (or dehydrant), such as sodium dodecyl sulfate (SDS), which is typically included in the buffer, or any combination thereof. Lysate solubilization may also be assisted using vigorous mixing, shearing, heating in surfactant, cavitation, bead beating, boiling, degassing, or any combination thereof.

"Solubilizing", as used herein with reference to a cell suspension, refers to the ability to disaggregate either partially or fully and make cellular components soluble in the lysis buffer.

As used herein, the term "analysis" refers to a process for determining the identity or nature of molecular components of an organism. In certain embodiments, the analysis identifies patterns or signatures for identifying a biological or chemical entity.

As used herein, the term "physical change" refers to the process of effecting a change in the biological sample in terms of the nature and size of its constituents, and includes without limitation, the process of lysing cells, reacting chemical species to make them smaller or larger, breaking up chemical complexes to form smaller constituents. Accordingly, such "physical" changes include the formation of products of a chemical reaction, as well as the deformation of constituents of the sample, such as cells and biological complexes.

As used herein "sonic energy" refers to energy produced by either a sonication device such as a sonication probe, or an ultrasound transducer capable of producing ultrasound waves.

Although the following systems and methods are described as being applied primarily to lyse or break open biologic species and solubilize the proteins/nucleic acids, those skilled in the art will appreciate that the disclosed systems and methods can be used to lyse and solubilize substantially any type of cell component. In addition the system may be use as a reaction vessel to perform mixing and/or heating at a range of temperatures to perform chemical and enzymatic reactions, synthesis of reactants form chemical monomers, such as organic chemicals, and polymers, including but not limited to DNA, proteins, alkyl hydrocarbons, methacrylate, and acrylate polymers, and drug moieties. This method is not limited to the bench top application, and can be made to be useable by technicians in the field, such as field technicians investigating white powder incidents and also crime science for fast processing of samples.

FIGS. 1 to 4 illustrate a lysing system 10 according to a first embodiment of the invention. The parts of the system are shown separated in FIGS. 1 and 2, and basically comprise a vial 12 having an internal chamber 14 for receiving a sample, the vial having an open upper end 15, a plug or insert 16 for sealing the open upper end 15 of the vial or chamber, a retaining cap 18 for holding the plug in the vial, and a sonication head 19 for applying ultrasonic waves to a sample in chamber 14. A heater 20 surrounds the lower end of the vial for heating the contents of the chamber. The vial, plug and cap, when assembled as in FIGS. 3 and 4, form a tight gas and liquid sealed container, impervious to the escape of gas and liquid under high temperature, high pressure, or both.

The plug 16 has an enlarged head 22 at its upper end for seating against the upper end of the vial and a reduced diameter, elongate plunger or piston of predetermined length for extending into the chamber in order to pressurize the contents of the chamber. A pair of spaced annular grooves are provided on the outer surface of the plug for receiving O-ring seals 25 which seal against the inner surface of the vial as the plug is forced into the vial. The O-ring seals are made of a suitable heat resistant, resilient material such as rubber or a synthetic rubber such as Viton®, manufactured by Dupont De Nemours of Wilmington, Del. Although O-ring seals are illustrated in the exemplary embodiment, the seals may instead be permanently attached to the plug.

The cap 18 has internal threads 26 for threaded engagement with corresponding external threads 28 on the outer surface of the vial to secure the plug in the chamber. A flat inner end surface 29 of the cap acts as an abutment surface which engages with the head 22 of the plug to force it into the vial as the cap is screwed onto the vial. The outer surface of the cap may be smooth or may be provided with gripping ridges or other roughening to facilitate gripping and turning of the cap for tightening or loosening purposes.

Although the cap is secured on the vial by threaded engagement in the illustrated embodiment, the screw threads may be replaced in alternative embodiments by any other suitable fastener arrangement, such as a bayonet-type twist lock connection. The cap restricts rotation of the plug as it is pressed down into the vial, reducing wear on the O-ring seals, and assists in fully inserting the plug in the vial chamber in order to provide the desired pressure. However, in alternative embodiments of the invention, where rotation of the plug is not a problem, the plug may be formed integrally with the cap as an extension from the inner surface 29 of the cap.

The vial, plug and cap are preferably all of the same material to avert any gaps caused by disparate thermal expansion and contraction coefficients. In certain embodiments, the material for the plug expands at a greater rate than that of the vial, which increases the sealing ability as the temperature increases. The material selected must also be relatively rigid and strong to maintain its integrity and shape under high pressure conditions. O-rings are preferable for sealing the plug surface, to maintain a stiff plug yet have a deformable surface to mate with the vial. The material must also be selected to withstand the extreme temperature ranges common in thermal lysis. The presently preferred material is PEEK (Polyetheretherketon) although PC (polycarbonate), PMMA Polymethylmethacrylate), Acrylic, PDMS (Polydimethylsiloxane), and Polyolefin (ZEONOR®, Zeon Chemicals, Louisville, Ky.) are also suitable. The plug, vial and cap may be made by injection molding.

The heater 20 in the illustrated embodiment is a coil of resistive heating wires wrapped around the outer surface of the vial adjacent the contained sample. Other types of heating device may be used in alternative embodiments. The heater may alternatively comprise a block heater, RF induction heater, microwave heater, or the like.

In the illustrated embodiment, the inner surface of the vial is cylindrical and of uniform diameter along the majority of its length from the open end, with a reduced diameter portion 30 adjacent the lower end of the vial for receiving a sample to be processed, The lower closed end 32 of the chamber is conical in shape, for increased strength under pressurized conditions, and also to make processed sample recovery easier. In an alternative embodiment, the interior surface of vial may have a tapered section. The tapered section is formed such that the interior diameter of the tube is greatest at the open end and that the tube wall inclines to increasing thickness with increasing distance from the aperture. The plug will be shaped and dimensioned for mating with the tapered section. A cooperative fit between the sealing insert and the tapered section below the aperture aids in maintaining a tight seal between the sealing insert and the tube during compression.

The purpose of the plug is two-fold. First, it is designed to seal the chamber so that the sample is not lost in processing. Second, it creates and maintains pressure in the chamber during heating and/or sonication. The length of the plug is selected in order to give an initial pressure to the chamber. The length of the plug must be at least 1/2.5 of the chamber length. This will create an initial pressure of 2.5 atmospheres in the chamber. The length of the plug can be increased if greater initial pressures are desired, according to the following relationship:

$$(P1*V1)/(n1*R*T1)=(P2*V2)/(n2*R*T2)$$

where P is pressure, V is volume, n is the number of moles, R is a constant, and T is temperature. R is a constant and can be eliminated from both sides of the equation. Similarly we assume that the number of moles does not change (this is not exactly true, but the error will only increase the pressure during heating). So that leaves us with:

$$(P1*V1)/(T1)=(P2*V2)/(T2)$$

In an example where the initial pressure is 1 atm and final needed pressure is 25 atm., the initial temp is 20° C. and final temp is 200° C., $$2/V1=(1\ \text{atm}/25\ \text{atm})*(200°\ \text{C.}/20°\ \text{C.})=1/2.5$$

Alternatively, the plug can be constructed to be longer in order to reach higher pressures for other processing. The minimum plug length needed for heat lysis is 1/2.5 and the maximum length is to the top of the sample. One reason to use a longer plug is when lysis is performed with sonication and no heat. The pressure acts to contain the sample and reduce bubbling. The higher the pressure, the less sample that can be contained in the compressed air. The sample plug has been designed to withstand pressures up to 500 psi and this pressure can be achieved through any combination of mechanical force, heat, additional air volume, or any of the three alone.

The system of FIGS. 1 to 4 is described below as used for lysing cells in a biological sample, and the vial, plug and cap may be designed as an inexpensive single use item which is discarded after use. However, it will be understood that the system may be used for any chemical or biological process where a sample is to be processed using pressure, heat, and/or sonication either individually or in combination.

The vial in the illustrated embodiment is cylindrical with a cylindrical inner chamber. However, the vial and chamber cross-sections may be oval, oblong, rectangular, polygonal, or other shapes, with the cross-sectional shape of the plug matching that of the chamber for smooth sliding engagement in the chamber.

The vial, chamber, and plug dimensions are dictated by the sample size. The sample size may be of in the range of 1 microliter up to 10 milliliters in volume. It should be understood that the systems described herein are specially adapted to a small sample size such as this, as will be more fully explained below. A vial having a chamber of the order of 0.25 inches diameter and one inch length will accommodate samples of up to 100 microliters in volume, but the range of vial chamber length may be from 0.75 inches to 4 inches, depending on desired sample size. The plug or plunger length will be at least one half of the overall length of the vial chamber in order to produce a 2× compression of the air in the chamber before heat is applied. The dimensions will be selected such that the chamber dimensions when the plug 16 is fully inserted are sufficient to hold a sample of the desired volume with the desired gap between the upper surface of the sample and the lower end of the plug. The cap dimensions will be dependent on the vial outer diameter and the cap outer diameter may be in the range of 0.25 inches to 1.5 inches. The system can be used in a lysing method or other sample processing methods according to exemplary embodiments of the invention.

The pressurization reduces the bubble development and evaporation. Bubbles are formed during boiling and also during sonication. Such bubble formation can lead to a variety of problems in conventional sonication systems that mostly adversely affect yield, such as aerosolation and denaturation of active biochemical species due to formation of an air-liquid interface surrounding the bubble. By minimizing bubble formation, much smaller sample volumes (down to 1 microliter) can be processed without loss of sample. Pressurization also reduces the amount of water vapor or sample soluble in the compressed air, which also allows for the processing of smaller sample volumes.

Suitable biological samples for processing in the method of this invention include a biological material in any type of solvent. The preferred solvent for the sample is water, which is most compatible with further processing steps. Almost any composition of biological material and organic solvent can be used to form a suitable biological sample fluid. The amount of biological material in the biological sample fluid can be as low as one spore in a fluid sample having a volume of from about 10 microliters to 1 ml. The weight percent of biological material in the biological sample fluid can be as high as 100 percent, i.e. the solvent comprising water in the biological material. Typically, the weight percent of the biological material is in the range of from about 0.00000001 percent, up to about 10 percent, and preferably in the range of from about 0.00001 percent, up to about 1 percent. Although a variety of additional components may be included in the biological sample fluid, for example water, salts, buffers, and contaminants, in certain embodiments the biological sample fluid consists essentially of biological material and a suitable solvent. In other embodiments, the biological sample fluid consists essentially of biological material, buffer and water. In certain preferred embodiments, the biological sample fluid contains a high concentration of organic solvent. In other preferred embodiments, the biological sample contains a high concentration of water. As used herein, the term "high concentration" refers to a composition comprising more the 30 weight percent of a specified component based on weight of the composition.

The method may be used, for example, for lysing a cell or spore of any origin, e.g., prokaryotic or eukaryotic, such as bacterial cells, mammalian cells, yeast cells, insect cells, plant cells, viruses or spores. The criteria for employing conditions such as pH, buffer, ionic strength are known to the person skilled in the art, and are essentially the same as those used in conventional sonication procedures.

The methods described herein can also be used to perform high throughput synthesis of novel chemical moieties in small volumes, due to the potential of performing low volume mixing, and high temperature heating, in the absence of boiling or bubble formation, due to the pressurized vessel. In addition, the reaction chamber can be filled with any gas, reactive or non-reactive, oxidizing or non-oxidizing. Suitable gases for this purpose can include but are not limited to reactive gases such as bromine, chlorine, oxygen, or inert gases such as nitrogen or helium. Other reactant or catalyzing agents, can include polymer radical initiators, and enzymes, The biological samples may be derived first from other, well-known methods of preparing and analyzing biological materials. These methods are capable of determining, for example, the composition of a biological sample in terms of protein, amino acids, DNA, mRNA, oligonucleotides, polysaccharides, or any combination thereof. Such determinations can be correlated to a compositional database for identifying the origin of the sample, whether having a natural origin (e.g. an organism such as a bacteria or virus), an unnatural origin (e.g. a synthetic compound or genetically-engineering organism), or a combination of both.

The sample 33 to be lysed is placed in the bottom of the lysis chamber 14. This is the recessed portion of the vial, and can handle sample volumes as small as from 1 microliter to 0.5 mL depending on the sample vial geometry. The shape of the bottom of the vial is kept conical to make it easy to remove the sample after processing. Conical, spherical or tapered geometries will help to contain small sample volumes.

Figure 4:
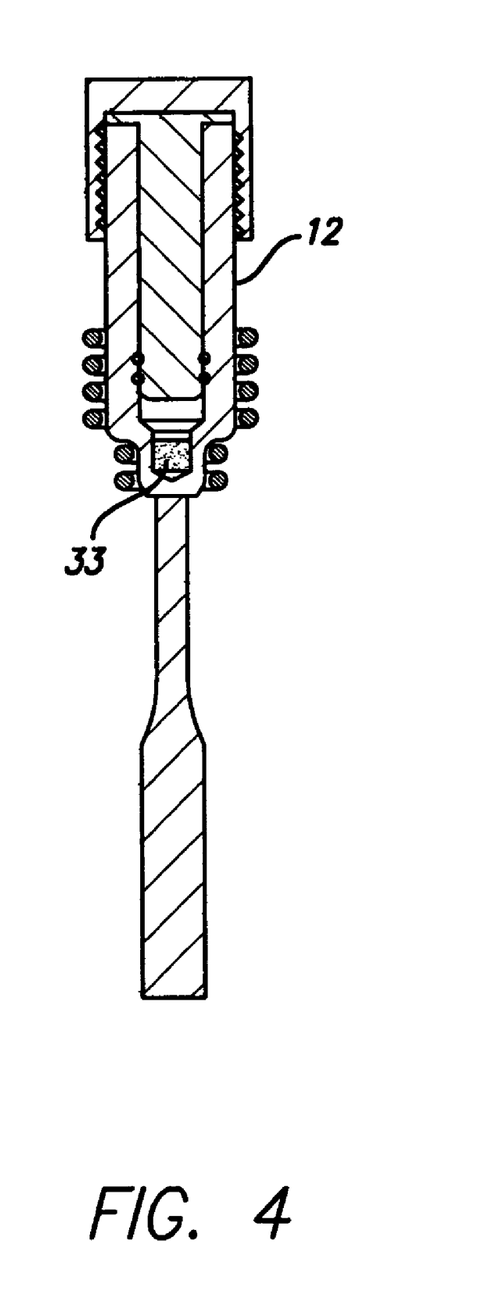
FIG. 4 is a cross-sectional view on the line 4-4 of FIG. 3.
Figure 5:
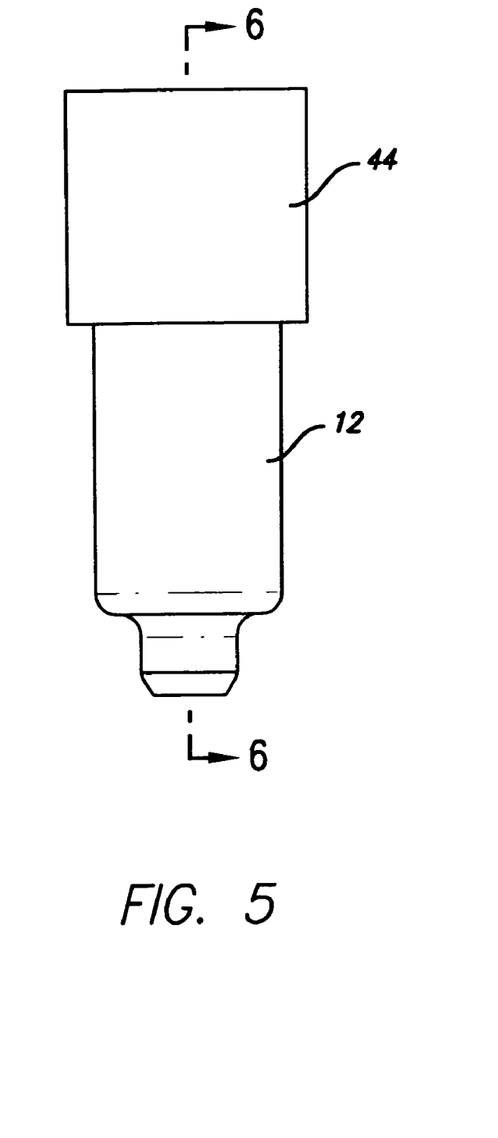
FIG. 5 is a side elevation view similar to FIG. 3 illustrating a modified system according to another embodiment of the invention which allows a sonication probe to be inserted into a sample.
Figure 6:
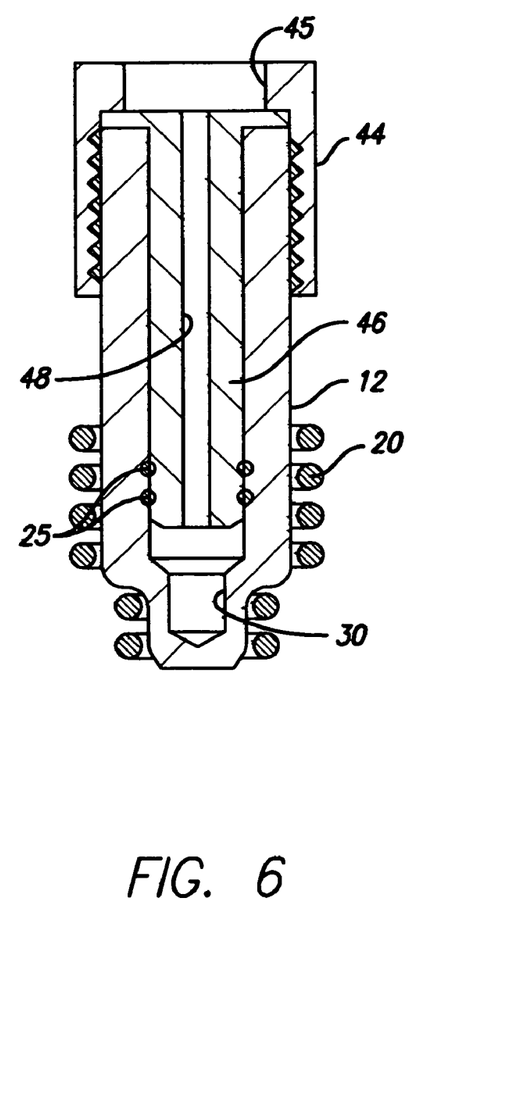
FIG. 6 is a cross-sectional view on the line 6-6 of FIG. 5.
Figure 7:
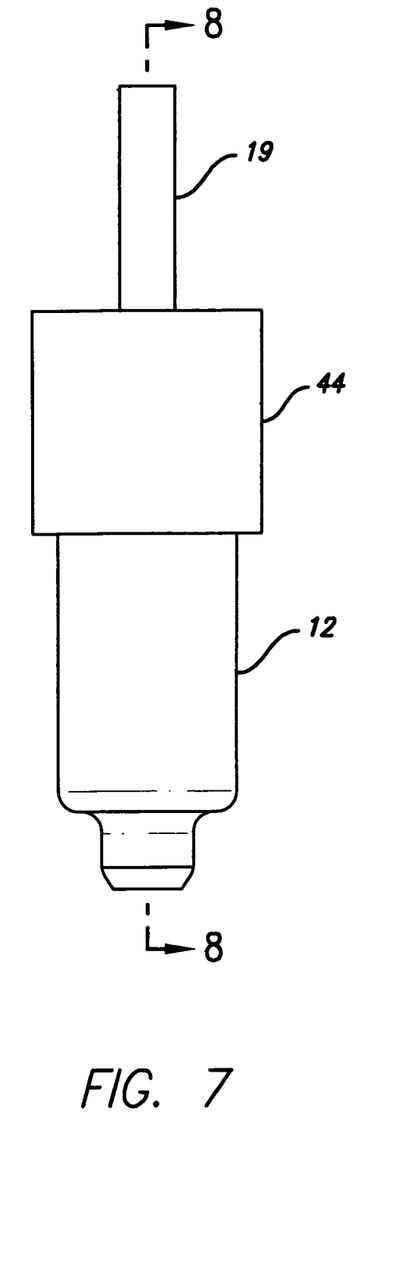
FIG. 7 is a side elevation view similar to FIG. 5 illustrating a sonication probe in position.

Once the desired sample for processing has been prepared, it is placed in the sample chamber 14 in the vial 12, and the plug or plunger 16 is inserted fully into the vial. The cap is screwed down over the upper end of the plunger to secure the plunger in place as illustrated in FIG. 4. The O-ring seals 25 create a pressure seal with the inner surface of the vial when the system is assembled as illustrated in FIG. 4. Although two O-ring seals are used in the illustrated embodiment, a greater or lesser number of seals may be used in alternative embodiments. The O-ring seals can withstand pressures up to 500 psi at temperatures up to 250° C.

The sample 33 is then heated to a desired temperature. The temperature may be in the range from 100° C. up to 250° C., depending on the species to be lysed, and in an exemplary embodiment the temperature used is in the range of 150° C. up to 200° C. As the temperature of the sample is increased to 200° C., the pressure inside the well increases to 24 atm, or 350 psi. This increases the boiling temperature to above 220° C., thus preventing boiling, but does not interfere with achievement of lysis. At the same time, the sonication head may be activated to subject the sample to ultrasonic waves. The lysing process is completed rapidly in around 5-10 minutes. This method provides the ability to perform bio-contained sample preparation with a variety of solvents and buffer combinations, of any molecular structure.

The method employs a combination of pressure with sonication (which may cause the sample to heat up due to sonic forces) and optionally with additional heating for lysing samples, using elevations of all three variables in exemplary embodiments in order to lyse small sample volumes. Various protocols may involve application of any two variables, i.e. sonication, heat, and/or pressure to achieve lysis. Application of sonication on small sample volumes cannot be done at atmospheric pressures because the entire sample is vaporized. Pressure can be combined with temperature alone to perform the lysis. Advantageously, sonication, elevated temperature and pressure are combined to sonicate small volume samples. The combination of the three allows lysis to be completed at lower temperatures than could otherwise be necessary, reducing the risk of destroying DNA strands. The increased pressure will prevent boiling of the sample and reduces creation of bubbles as a result of the application of heat or sonication, allowing smaller samples to be processed. The sonication allows lysis to be performed at a lower temperature than would be required if heat alone were applied to the sample, and is therefore important in the recovery of complete DNA strands and stability. Lower temperatures allow smaller samples to be processed. By varying the pressure, temperature, and sonication frequency and amplitude, the size of the DNA fragments extracted during lysis can be controlled.

The method of this invention is particularly useful for lysing of more robust biologicals such as spores. Temperature alone is not enough to lyse spores or other robust species without addition of chemicals to assist in the lysis. Temperature and pressure combined, with addition of sonication to allow the temperature to be reduced as noted above, makes it easier to lyse robust species while still retaining DNA and proteins. The temperature used will be species-dependent. For vegetative cells which are fairly easy to lyse, the temperature may be at the lower end of the range, while it will be higher for more robust species.

Figure 8:
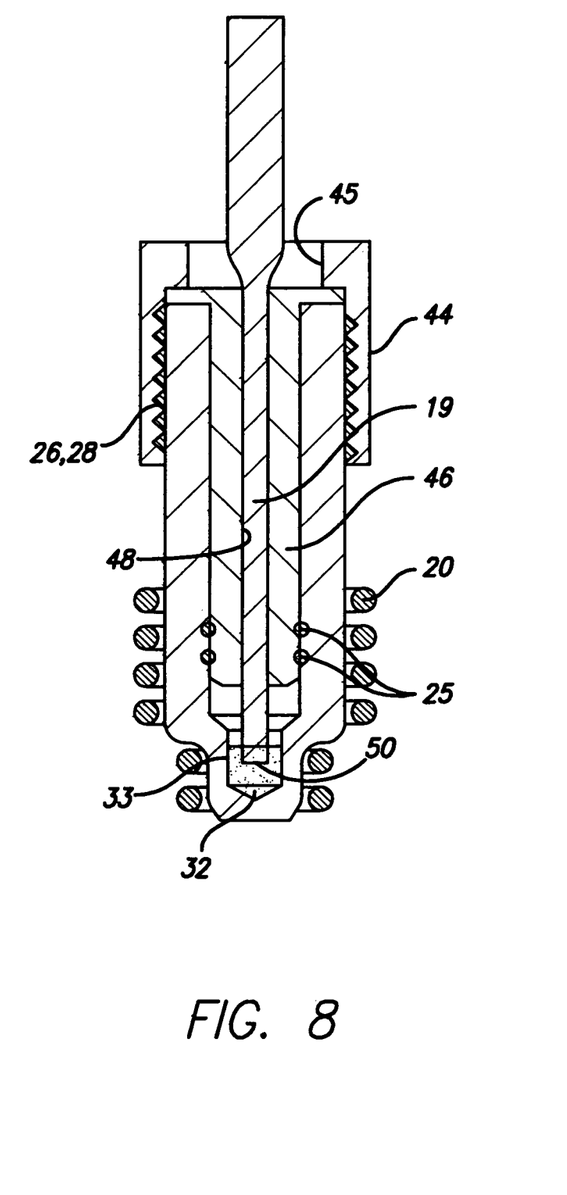
FIG. 8 is a cross-sectional view on the line 8-8 of FIG. 7.

In the embodiment of FIGS. 1 to 4, a sonication probe is placed against the lower end of the vial in order to subject the sample to ultrasonic waves. Alternatively, in the modified lysing system of FIGS. 5 to 8, the sonication probe comes into direct contact with the sample 42. In this embodiment, the locking cap 44 has a central opening 45 and the plug 46 has a through bore 48 through which the probe 19 is inserted so that the tip 50 of the probe comes into contact with the sample 33, as illustrated in FIG. 8. Other parts of the system of FIGS. 5 to 8 are identical to those of the previous embodiment, and like reference numerals have been used for like parts as appropriate.

In the modified system of FIGS. 5 to 8, two separate pressure seals are required. The first is the double O-ring seal 25 between the plug or plunger 46 and the inner surface of the vial 12. The second is between the sonication probe 19 and the passageway or through bore 48. The sonication probe should be sealed to the plug before the plug is sealed to the bore. This seal allows the pressurization to occur as the plug is inserted, so that the sample is still contained and aerosolization is prevented. Since the sonication probe does come into contact with the sample prior to lysing, it will need to be thoroughly decontaminated before reuse.

The through-bore 48 may be used to add or remove sample from the vial, prior to or after insertion of the probe 19. More than one through-bore may be provided if desired; for example, for insertion of a pressure monitor into the sample chamber. The second seal between the probe and/or temperature bore 48 may be a pressure seal such as an O-ring or the like, or the probe may be permanently sealed in the bore with epoxy or other glue. If one or more additional through bores are provided, for example to allow addition or removal of material, these will be sealed during lysis. The extra fluid connections can transform the system into a reaction vessel where multiple processes can take place. For example, the sample can first be lysed using the method described above in connection with FIGS. 1 to 4, at the desired temperature, pressure, and sonication frequency and amplitude. After lysis is complete, additional solutions can be added to the lysate to prepare the sample for labeling. Finally, a reactive dye can be added to the sample to produce analysis-ready samples. All of this can be accomplished in a discrete volume at various pressures and temperatures, and sonication can be added to improve mixing of the constituents.

Instead of inserting the probe 19 through passageway or bore 48, it could instead be applied externally as in the first embodiment, with the passageway 48 either sealed during lysis or used for insertion of a temperature or pressure monitor into the sample chamber. The passageway may then be used as a fluid passageway for addition of other solutions or materials to the sample after lysis, as discussed above.

Figure 9:
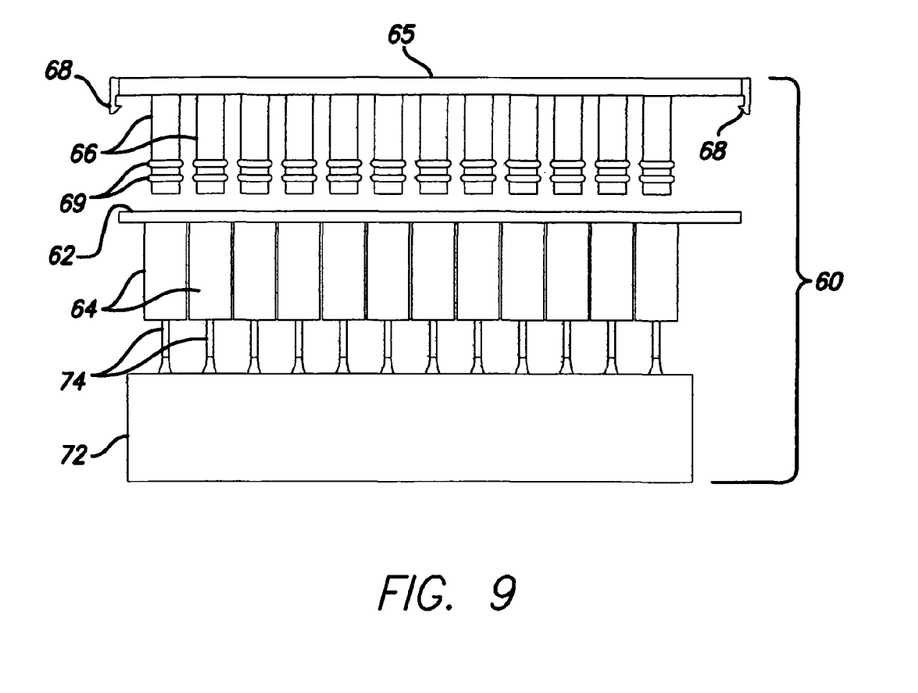
FIG. 9 is an exploded side elevation view of the components of a multi-well lysing system according to another embodiment of the invention.
Figure 10:
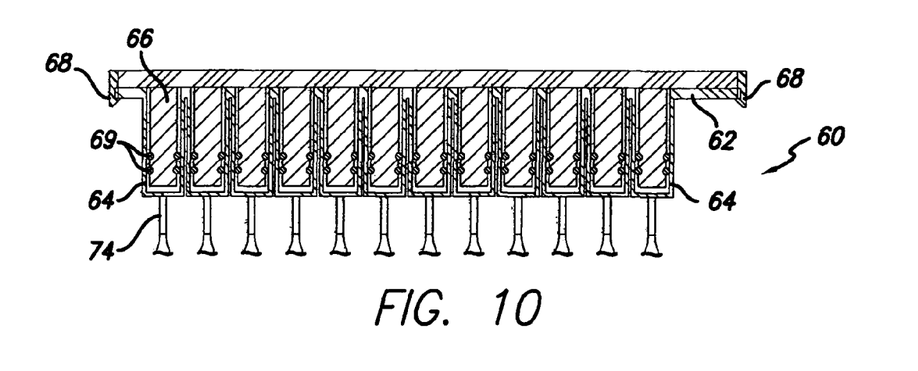
FIG. 10 is a cross-sectional view of the multi-well and plug plates of FIG. 9 in an assembled condition.
Figure 11:
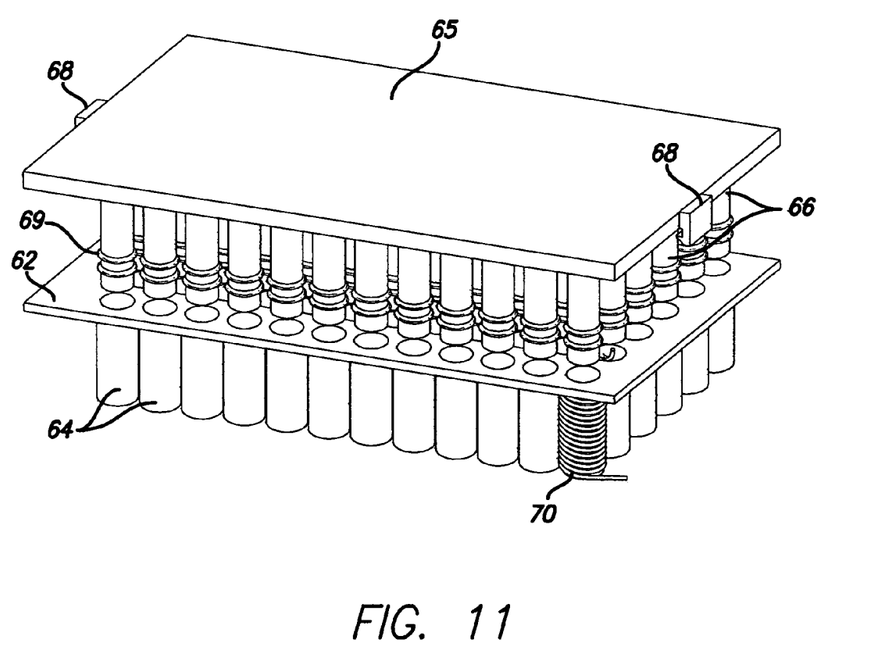
FIG. 11 is a perspective view of the multi-well plate and plug plate of the system of FIGS. 9 and 10.

FIGS. 9 to 11 illustrate a processing or lysing system 60 according to another embodiment of the invention which can process a plurality of different samples simultaneously. The system basically comprises a multi-well plate 62 having a plurality of wells or chambers 64 each for receiving a sample of predetermined size, a plug plate 65 having a plurality of plugs or plungers 66 projecting from one face for sealing engagement in a respective aligned well in the multi-well plate, as illustrated in FIG. 10, and a locking or latching mechanism 68 for securing the two plates 62 and 65 together when each plug is fully inserted in the respective well. The locking mechanism may comprise clip locks as indicated, or the two plates may be secured together by spaced screw fasteners around their periphery, or by any other suitable securing or clamping mechanism.

In an exemplary embodiment of the invention, the multi-well plate 62 is a 96 well plate, and the plug plate has a corresponding number of plugs. The dimensions of each well and the corresponding plug are selected in the same way as described above for the single sample system of FIGS. 1 to 4, depending on the desired sample size and the desired pressurization. The plug length is suitably sufficient to produce at least 1/2.5 reduction in the air volume in each chamber, and the sample sizes may be of the order of 1 microliter to 1 milliliter. Each plug has a pair of annular grooves adjacent its tip and O-ring seals 69 are mounted in the grooves for sealing engagement with the wall of the well when the plug is forced into the well.

The dimensions of the 96 well plate, the layout of the wells, and the well diameters may be the same as for a standard 96 well sample tray. This makes it easy to transfer samples from the standard tray to the 96 well lyser plate, without specialized equipment. This will allow cross use of the plug plate 95 with standard plates, providing the user with the ability to contain and partially pressurize the sample.

A suitable heater 70 is provided for heating the sample in each well. This may be a block heater or heating coils similar to the heater 20 of FIG. 1 around the outer surface of each well as shown by way of example around one of the wells in FIG. 11. An ultrasonic device 72 having a plurality of tips or heads 74 equal to the number of wells in the plate is used to apply ultrasonic waves to the sample in each well. A suitable multi-tip ultrasonic probe for this purpose is manufactured by Misonix, Inc. of New York, such as the Misonix 96 Probe Horn.

The multi-well plate and plug plate may be made of the same material as the single chamber vial, plug and cap. The presently preferred material is carbon doped PEEK (Polyetheretherketon) although PC (poly carbonate), PMMA (Polymethylmethacrylate), Acrylic, PDMS (Polydimethylsiloxane), and Polyolefin (Zeonor®) are also suitable. Carbon doped PEEK can be routinely heated to a temperature above 200° C. This material has the additional advantage that, when used to injection mold various components, it is bio-compatible, meaning that it does not interact with proteins or nucleic acids. Such a plate will also withstand vibration or agitation, as is produced by an ultrasonic wave generator. Standard multi-well plates are made of polycarbonate, but this melts at low temperatures, not permitting the high temperatures needed for lysis of spores. However, eukaryotic cells can be lysed at lower temperatures, so a standard 96 well plate may be suitable for use as the plate 62 in a lysing apparatus for such materials.

The plug plate must be constructed to be sufficiently rigid to compress all of the 96 wells equally. As noted above, the plug plate and integral plugs may be injection molded from carbon doped PEEK or the like, and the plate 64 may be thicker than the multi-well plate for added rigidity, as seen in the drawings.

The method using the multi-chamber lysing apparatus of FIGS. 9 to 11 is essentially the same as the single vial method described above. Samples are first placed in the wells or chambers 64, and the plug plate is aligned over the multi-well plate and lowered until each plug enters the aligned well, pressurizing the chamber. The two plates are secured together by latches 68 or other suitable fastener devices such as screws. The wells are then heated and the multi-probe sonication device 72 is aligned with the lower ends of the wells and moved towards the wells until each probe 74 contacts the bottom surface of the respective aligned well, as illustrated in FIG. 10. In an alternative embodiment, the apparatus may be modified to allow the probes 72 to enter the sample chamber through the plug plate and respective plugs, in a similar manner to the single vial apparatus of FIGS. 5 to 8. Alternatively, with the external sonication probe arrangement of FIG. 10, other fluidic inputs to the 96 wells may be provided through the plug plate, such as sealable connecting conduits to allow additional materials to be supplied to the respective chambers or wells, or to allow a processed sample to be removed from each well for further testing or processing.

The method of the present invention combines heat, sonication and pressure in order to provide novel processing capability of one or more samples contained in sealed sample chambers. Temperature control allows chemical reaction rates to be controlled and assists in diffusing or solvating the liquid constituents quickly. Introduction of ultrasonic waves or sonication adds non-thermal energy which assists in the breakdown of robust species, and also assists in the solvation of samples, and also can assist in mixing of materials in the sample, if necessary. However, prolonged sonication can cause the temperature of the biological sample to increase over time. Pressurization of the sample chamber prevents boiling at high temperatures and the loss of low volume samples. Any two of these variables can be used in combination, but the preferred method is to use all three in combination.

In the apparatus and method of the above embodiments, tight control of the process can be maintained which allows the optimization of sample processing for a specific set of analytes which may have specific limitations or characteristics which may require such control. An example is the processing of biological samples and tissues which contain a multiplicity of macromolecules. These individual structural macromolecules have a range of individual bond strength between atoms, which make some molecules more or less stable under a variety of conditions. In particular, the stability of the peptide bond in native proteins is considerably higher than the phosphodiester bonds of the primary DNA sequence. As a result, the integrity of the primary amino acid peptide bond is significantly more stable at high temperatures (greater than 150° C.) than the phosphodiester bond of DNA. This difference presents significant challenge when processing such agents, such as biological spores, for analysis. In order to achieve complete thermal lysis and solubilization of these agents, the optimal temperature range (without introduction of ultrasonic energy) is between 195 to 220° C. Under these conditions, the protein species remain intact, while the primary DNA structure becomes unstable and fragments to sizes between 0-300 bases in length. The short length of these DNA sequences makes analysis difficult. A better method is to control all elements of the reaction to prevent breakdown of DNA, while accomplishing the complete lysis of the sample being processed. In this invention, the application of heat, ultrasonic energy, and high pressure to the sample can be optimized so that lysis and solubilization of biological species can be completed at lower temperatures, without breakdown of the DNA. This has the added advantage that the process allows for analysis of both the proteome and the genome from the same sample. This is important because the sample size available for analysis is often limited to small quantities.

The pressurization of the sample in a sealed chamber reduces the occurrence of bubbles (which can interfere with subsequent assay procedures) and evaporation or loss of sample. Bubbles can be formed through heating or boiling or as a result of vibration induced by sonication, and increasing the pressure will reduce both of these effects. By minimizing bubble formation and evaporation, much smaller sample volumes can be processed than was possible in the past, down to 1 microliter, without loss of sample. Pressurization also reduces the amount of water vapor or sample soluble in the compressed air in the chamber, which also permits processing of smaller samples. The sample processing takes place in a completely bio-contained device, which reduces the safety hazard generated by aerosolization of potentially hazardous biological samples.

The solubility of liquids is increased at higher pressures as are used in the method and apparatus of this invention, so that higher concentrations of reagents can be used during sample processing. As the pressure is increased, the sample will contain more dissolved gas particles. Any of the sample that does evaporate is more likely to rejoin the sample at higher pressures.

This system and method enables researchers and other interested parties to make lysates or a solubilized mix of proteins, DNA, and any other extracellular or intracellular macromolecules from variety of organism and cell types, including viruses, bacteria (prokaryotic), bacterial spores, plant cells, and eukaryotic (such as mammalian) cells. The method is particularly versatile when a controlled combination of pressure, temperature, and sonication is used, and the conditions are optimized for the particular sample to be processed. When used for lysing, the method provides extracts of proteins and nucleic acids in an amount sufficient to allow further characterization or experimentation with such cell components.

EXAMPLE

Preparing Lysate from *Bacillus* sp. Spores

Figure 1:
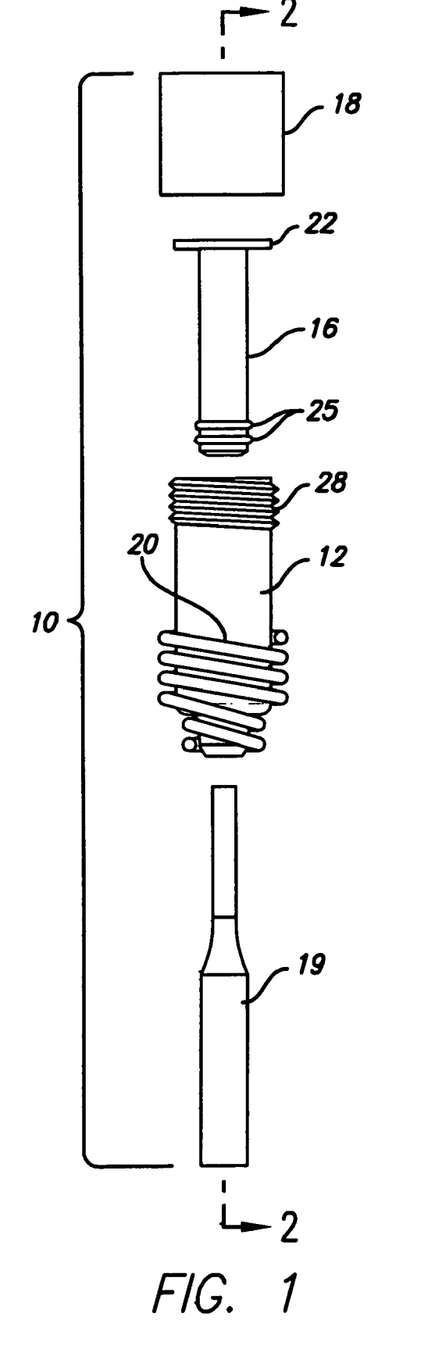
FIG. 1 is an exploded side elevation view of the components of the system according to a first embodiment of the invention.
Figure 2:
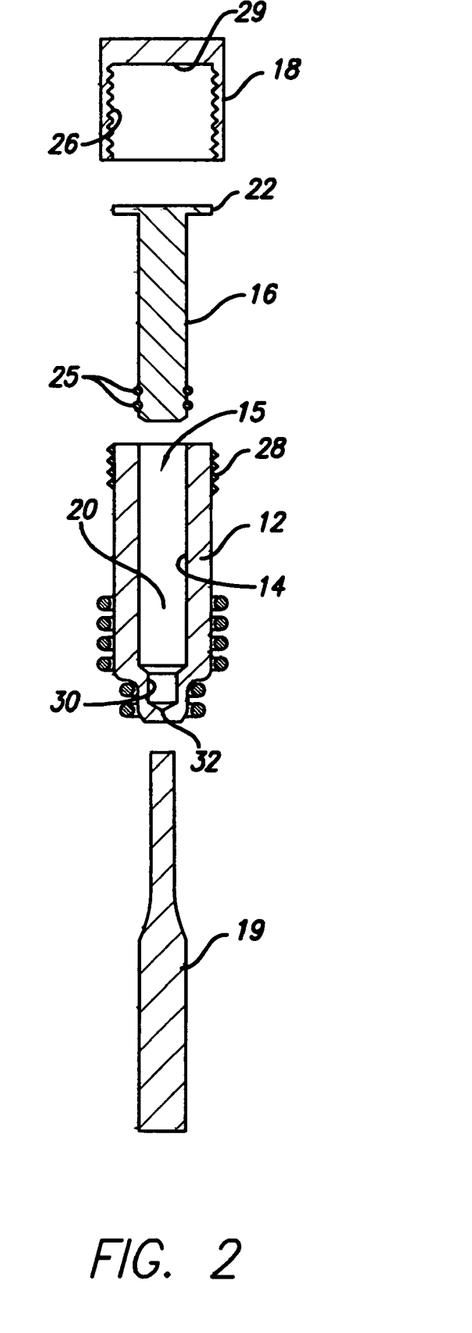
FIG. 2 is an exploded cross-sectional view of the components on the line 2-2 of FIG. 1.
Figure 3:
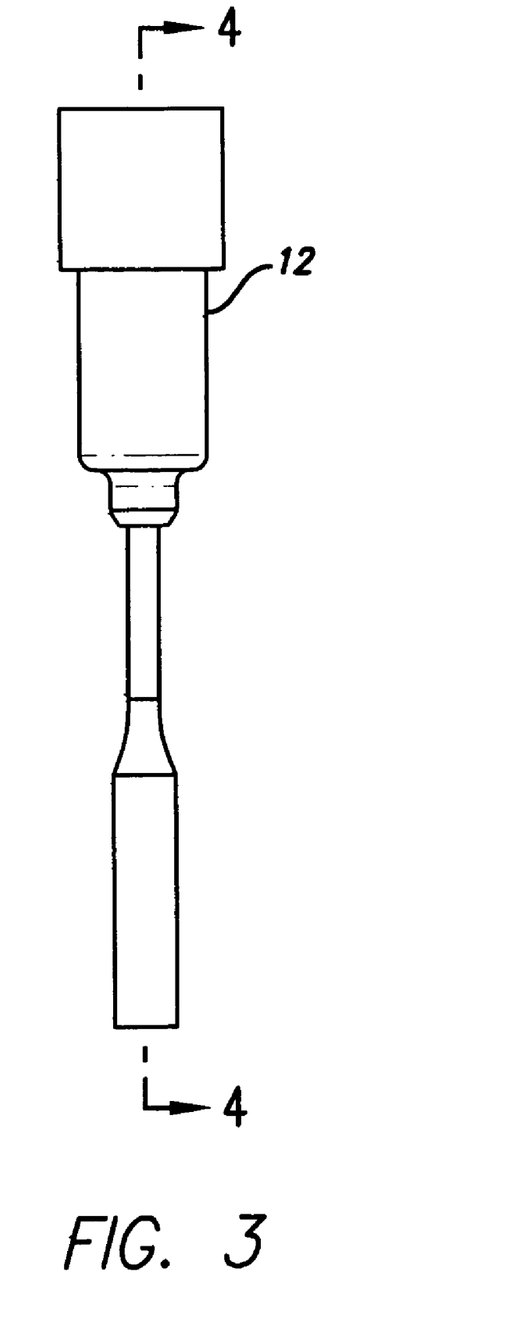
FIG. 3 is a side elevational view illustrating the system of FIGS. 1 and 2 assembled and ready for use.

A system essentially as depicted in FIGS. 1 and 2 was used to lyse a suspension of spores from *Bacillus* sp. A disposable collection vial was used for both sample containment and lysis. The vial was inserted into a thermal controlled well, and the temperature was raised to 95° C. The vial was pressurized to approximately 100 PSI, and the sample was pulse sonicated (10×, 3 second cycles, over 1 minute) at four different power levels (5.5 watts, 16.5 watts, 33 watts and 49.5 watts). Using a 40× objective microscope, the samples were observed to contain decreasing amounts of in-tact spores as the power was increased. At the highest power level, the samples contained virtually no in-tact spores.

Figure 12:
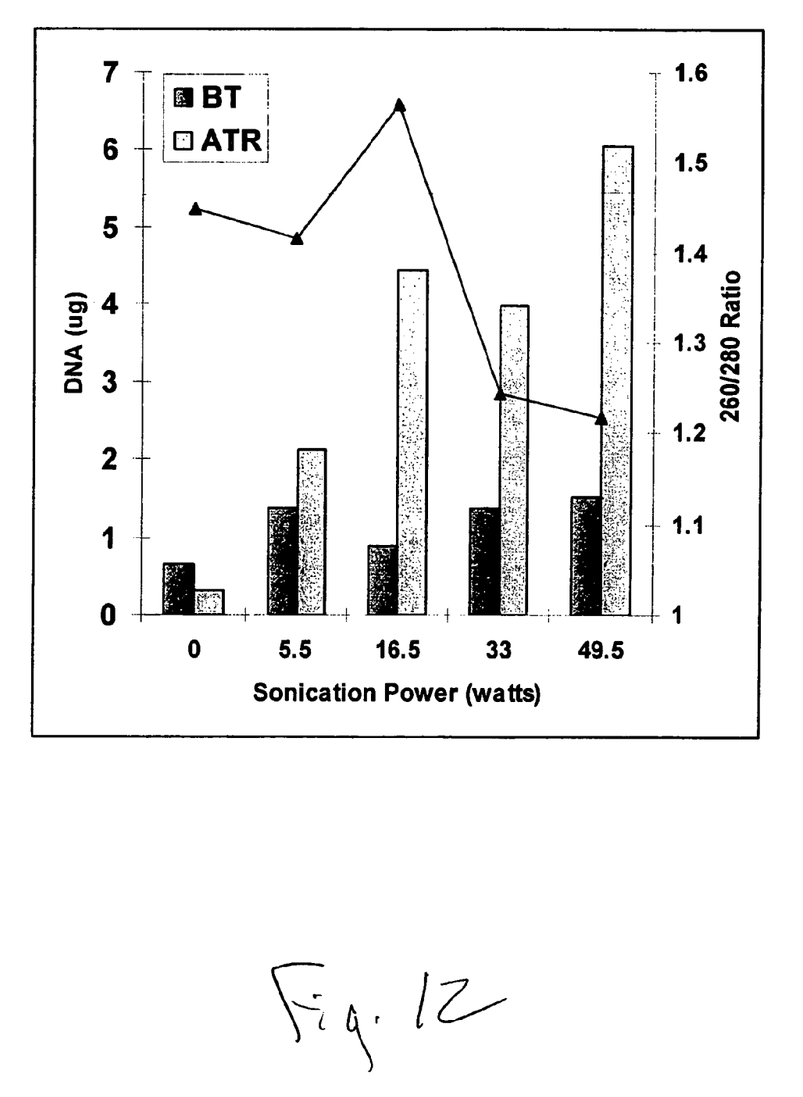
FIG. 12 is a graphical representation of the results of the Experiment described below.

Aliquots of each sample were taken after treatment, and the DNA was analyzed using 260 nm wavelength to assess concentration and 280 nm wavelength to assess integrity. The results are depicted in FIG. 12. (BT=*Bacillus thurengensis*, and ATR=*Bacillus atrophaeus*.) According to these results, an increasing amount of DNA is released as the power is increased. Additionally, the power setting of 16.5 appeared to be optimal for the generation of the greatest amount of in-tact DNA.

The information presented above is provided to give those of ordinary skill in the art with a complete disclosure and description of how to make and use the preferred embodiments of the invention, and is not intended to limit the scope of what the inventor regards as his invention. Modifications of the above-described modes for carrying out the invention that are obvious to persons of skill in the art are intended to be within the scope of the following claims. All publications, patents, and patent applications cited in this specification are incorporated herein by reference as if each such publication, patent or patent application were specifically and individually indicated to be incorporated herein by reference.

What is claimed is:

1. A system for effecting a physical change in a biological sample, comprising:
    a) a sample container having at least one rigid chamber for containing the sample, the chamber having at least one opening;
    b) a plug adapted for sealing the opening of the chamber and for applying pressure to the chamber, the plug having at least one O-ring seal mounted on the plug for sealing engagement with the chamber when inserted into the opening;
    c) a securing device for securing the plug in the chamber, and
    d) a sonication device for subjecting a sample in the chamber to sonication,
    wherein the rigid chamber is capable of maintaining its shape at a pressure within the chamber of from more than 30 psi up to about 500 psi.

2. The system as claimed in claim 1, wherein the chamber has a predetermined length and the plug has a length equal to about half the length of the chamber.

3. The system as claimed in claim 1, wherein the securing device comprises a cap, the cap and the sample container having interengageable formations for releasably locking the cap over the opening and securing the plug in the chamber.

4. The system as claimed in claim 3, wherein the interengageable formations comprise external threads on the sample container adjacent the opening and internal threads on the cap for releasable threaded engagement with the external threads on the sample container.

5. The system as claimed in claim 1, wherein the plug has at least one through bore and the securing device has an opening aligned with the through bore when the plug is inserted into the opening to provide access to the chamber.

6. The system as claimed in claim 5, further comprising a device inserted through the opening and through bore into the chamber, the device being selected from the group consisting of: the sonication device, a pressure sensor, a temperature sensor, and a fluid flow tube for supplying material to the sample chamber or removing material from the sample chamber.

7. The system as claimed in claim 1, wherein the sonication device comprises an external probe with an end secured in contact with the chamber opposite the opening.

8. The system as claimed in claim 1, wherein the plug has a through bore and the sonication device has a probe for insertion through the through bore and into the sample in the chamber, a seal being formed between the probe and the through bore.

9. The system as claimed in claim 1, further comprising a heater mounted adjacent the chamber for heating the sample to a temperature between 100° C. to 250° C.

10. The system as claimed in claim 1, further comprising a temperature sensor for monitoring temperature in the chamber, and a controller for selectively varying the temperature.

11. The system as claimed in claim 1, further comprising a pressure sensor for monitoring pressure in the chamber.

12. The system as claimed in claim 1, wherein the sample chamber further comprises a reduced diameter portion opposite the opening for containing the sample.

13. The system as claimed in claim 1, wherein the chamber has a diameter of approximately 0.2 to 0.3 inches and a length in the range from 0.7 to 4 inches.

14. The system as claimed in claim 13 wherein the plug has a length of at least half the length of the chamber.

15. The system as claimed in claim 1 wherein the chamber and plug are made of the same material.

16. The system as claimed in claim 15, wherein the material is selected from the group consisting of: polyetheretherketone, polycarbonate, polymethylmethacrylate, acrylic, polydimethylsiloxane, and polyolefin.

17. The system as claimed in claim 16, wherein the material is polyetheretherketone.

18. The system as claimed in claim 1, wherein the sample container further comprises a multi-well plate having a plurality of sample chambers, and wherein the system further comprises a plurality of plugs.

19. The system as claimed in claim 18, further comprising a cover plate for covering the openings of the sample chambers, the plugs being formed integrally with the cover plate and projecting from the cover plate for sealing engagement in the openings of respectively aligned sample chambers when the cover plate is secured over the multi-well plate.

20. The system as claimed in claim 19, wherein the securing device comprises a suitable fastener mechanism for securing the cover plate to the multi-well plate with the plugs extending into and pressurizing the respectively aligned sample chambers.

21. The system as claimed in claim 20, wherein each plug has at least one seal for sealing engagement with the sample chamber.

22. The system as claimed in claim 21, further comprising a heater assembly for heating samples in the chambers substantially uniformly.

23. The system as claimed in claim 1, wherein the rigid chamber is capable of maintaining its shape at a pressure within the chamber of from more than 30 psi up to about 350 psi.

24. The system as claimed in claim 1, wherein the rigid chamber is capable of maintaining its shape at a pressure within the chamber of from more than 30 psi up to about 100 psi.

* * * * *